(12) United States Patent
Bayerköhler et al.

(10) Patent No.: US 6,890,559 B1
(45) Date of Patent: May 10, 2005

(54) DIRECTLY COMPRESSIBLE RAW MATERIAL FOR TABLETS

(75) Inventors: Theodor Bayerköhler, Mannheim (DE); Hanspeter Degelmann, Worms (DE); Tillmann Dörr, Hohen-Sülzen (DE); Lutz Guderjahn, Worms (DE); Holger Janssen, Hohen-Sülzen (DE); Jörg Kowalczyk, Bockenheim (DE)

(73) Assignee: Sudzucker Aktiengesellschaft Mannheim/Ochsenfurt, Mannheim (DE)

( * ) Notice: Subject to any disclaimer, the term of this patent is extended or adjusted under 35 U.S.C. 154(b) by 272 days.

(21) Appl. No.: 10/070,662

(22) PCT Filed: Sep. 9, 2000

(86) PCT No.: PCT/EP00/08830

§ 371 (c)(1), (2), (4) Date: Jul. 9, 2002

(87) PCT Pub. No.: WO01/19208

PCT Pub. Date: Mar. 22, 2001

(30) Foreign Application Priority Data

Sep. 10, 1999 (DE) .......................................... 199 43 496

(51) Int. Cl.⁷ .............................. A61K 9/20; A61K 9/28

(52) U.S. Cl. ........................................ 424/464; 424/474

(58) Field of Search .................................. 424/400, 439, 424/464, 474, 484, 489, 499, 502, 69; 514/960, 951; 426/285

(56) References Cited

U.S. PATENT DOCUMENTS

| | | | | |
|---|---|---|---|---|
| 4,572,916 A | * | 2/1986 | Lindley et al. | 514/777 |
| 5,616,361 A | * | 4/1997 | Virtanen et al. | 426/658 |
| 5,958,471 A | * | 9/1999 | Schwarz et al. | 426/3 |

FOREIGN PATENT DOCUMENTS

| | | | |
|---|---|---|---|
| EP | 0 738 252 B1 | 10/1995 | C07C/31/18 |
| WO | WO 90/14821 | 12/1990 | A61K/9/16 |
| WO | WO 99/47532 | 9/1999 | C07H/15/04 |
| WO | WO 00/64916 * | 11/2000 | 15/4 |

* cited by examiner

*Primary Examiner*—Thurman K. Page
*Assistant Examiner*—Sharon Howard
(74) *Attorney, Agent, or Firm*—Finnegan, Henderson, Farabow, Garrett & Dunner, L.L.P.

(57) ABSTRACT

The present invention relates to an improved method of producing agglomerates and compressed products containing isomaltulose and/or hydrogenated isomaltulose.

18 Claims, No Drawings

DIRECTLY COMPRESSIBLE RAW MATERIAL FOR TABLETS

The present invention relates to a method of producing an agglomerated, free-flowing product of isomaltulose, isomalt and/or isomalt variants, compressed products produced from them as well as a method of producing these agglomerates and compressed products.

Compressed products are foods, drugs, or semi-luxury items consisting of compressed ingredients. Compressed products accordingly generally contain a carrier or diluent, binder, lubricant or parting compound as well as the active ingredients plus flavorings, pharmaceutical substances or sweeteners. Sucrose, lactose, glucose, starch or mannitol is often used as the carrier or diluent.

European Patent 0 028 905 B1 discloses tablets containing isomaltulose and methods of producing the same. This publication discloses an advantageous use of isomaltulose as a diluent for the production of compressed products, because isomaltulose can be pressed directly without the use of a binder and without controlled granulation. According to this publication, crystalline isomaltulose produced directly by enzymatic conversion of sucrose to isomaltulose is used for tabletting.

German Patent 196 39 343 C2 discloses compressed products containing isomalt and isomalt variants. These compressed products are produced by simple pressing of the individual ingredients without a special mechanical and/or chemical treatment of the individual ingredients.

European Patent Application 0 625 578 A1 discloses isomalt variants, but no compressed products containing these sweeteners.

The compressed products containing isomaltulose, isomalt and isomalt variants known from the related art are all characterized by the required use of comparatively high compression pressures in the production of the compressed product, but only a comparatively low tablet hardness can be achieved. In addition, the compressed products of the related art could also be improved with regard to their sensory properties; for example, they have a roughness when bitten into, and their fracture properties are not advantageous; furthermore, the dissolving properties in the mouth should also be improved.

The technical problem on which the present invention is based thus consists of a method of producing compressed products of isomaltulose, isomalt or isomalt variants which overcome the disadvantages mentioned above, and in particular a method that is capable of producing compressed products of a great hardness which are characterized by improved sensory properties and an improved fracture behavior while using the lowest possible compression pressures.

The present invention solves the basic problem on which it is based by providing a method of producing an agglomerated, dried and free-flowing product of isomaltulose, isomalt and/or at least one isomalt variant, wherein a solution or suspension containing isomaltulose, isomalt or isomalt variants is sprayed with a supply of dry air onto or into a powder of isomaltulose, isomalt and/or at least one isomalt variant, so that the resulting agglomerated product is subjected to a secondary drying and cooling, yielding an agglomerated, free-flowing and dried product. This invention also solves the technical problem on which it is based by providing a free-flowing, dried agglomerate that is produced by the present method as well as a method of producing a compressed product of a free-flowing agglomerate obtained as described above, wherein the agglomerate is mixed with additives and/or flavorings and then pressed.

According to this invention, an agglomerated free-flowing product is produced from one or more of the educts isomaltulose, isomalt or isomalt variant by spraying a solution and/or suspension of one or more of the educts with a supply of dry air onto or into a powder of isomaltulose, isomalt and/or isomalt variants. In an advantageous manner, this invention provides for a supply of a solution or a suspension and a powder of an identical educt, i.e., a supply of an isomalt solution or suspension to an isomalt powder, a supply of an isomaltulose solution or suspension to an isomaltulose powder and a supply of a solution or suspension of an isomalt variant to a powder of an isomalt variant. Following the spray drying thus performed, the resulting agglomerated product is subjected to a secondary drying and cooling, yielding an agglomerated, crystalline, free-flowing product. This dried, agglomerated, free-flowing product, which is also referred to as an agglomerate in the context of the present invention, is characterized by a good solubility, good spreadability, a low bulk weight and good compressibility. It is therefore an excellent starting material for the production of compressed products and is also the object of the present invention. The resulting agglomerate of isomaltulose, isomalt and/or one or more isomalt variants may be used, for example, as a sweetener or as a filler (bulking agent) in a compressed product, for example.

In a preferred embodiment of this invention, spray drying may be carried out to advantage according to this invention by means of a spray belt dryer comprising a spray tower which is arranged above a moving surface such as a cloth belt. In an advantageous manner in a preferred embodiment of this invention, the educt solution or suspension and the powder, preferably ground, especially a recycled powder, are sent separately from one another to the head end of a spray tower. Drying air is supplied in parallel flow with the former in an advantageous manner. The powder supplied serves as a crystallization base for the educt solution or suspension. The educt solution or suspension thus causes the powder to agglomerate. The powder and the sprayed educt solution or suspension are mixed and fall down the spraying tower together, both wetting one another and agglomerating, whereupon the water of the educt solution or suspension is evaporated, and a moist product layer is deposited on the cloth belt arranged in the lower part of the spray tower, and the resulting agglomerated product is transported to a downstream secondary drying and cooling zone. This transport may also be accomplished by means of a worm gear, for example. Evaporation and cooling of the agglomerate take place in the secondary drying and cooling zone.

In an especially preferred embodiment of this invention, secondary crystallization is performed, e.g., in a crystallization drum, after cooling.

In another preferred embodiment, this invention provides for the agglomerated, dried and free-flowing product obtained after cooling, optionally after performing the secondary crystallization step, to be ground at least partially, and in an especially preferred embodiment, the ground product is supplied as an educt back to the present process, i.e., it then functions as a carrier for the educt solution or suspension sprayed into it. A portion of the agglomerated free-flowing product is thus converted to a powder form and recycled back to the process. The milling may be performed in a mill, e.g., an air separation ball mill. In an especially preferred embodiment of this invention, the powder is milled to a particle diameter of 10 $\mu$m to 400 $\mu$m, especially 30 $\mu$m to 300 $\mu$m, most especially 50 $\mu$m to 200 $\mu$m. In conjunction with the present invention, a particle diameter of 30 $\mu$m to 300 $\mu$m, for example, is understood to mean that at least 90% of the particles ($d_{90}$) of the fraction have a diameter $\geq 30$ μm to $\leq 300$ μm.

In another preferred embodiment of this invention, the educt solution or suspension, i.e., the solution or suspension containing isomaltulose, isomalt or isomalt variants, has a dry solids content of 30 wt % to 70 wt %, preferably 60 wt % to 70 wt %. In another preferred embodiment of the present invention, the educt solution or suspension has a temperature of 50° Celsius to 90° Celsius, especially 65° Celsius to 80° Celsius.

In another preferred embodiment of this invention, the educt solution or suspension is sprayed into the powder with a spray pressure of 100 to 200 bar, especially 120 to 180 bar.

In another preferred embodiment of this invention, the quantity ratio of powder to educt solution or suspension is 1:1 to 3.5:1, preferably 2.5:1 to 3.3:1.

In another preferred embodiment of this invention, the temperature of the drying air is 120° Celsius to 180° Celsius, especially 140° Celsius to 160° Celsius. In another preferred embodiment of this invention, the temperature of the secondary and cooling air is 20° Celsius to 80° Celsius, especially 20° Celsius to 60° Celsius.

In another preferred embodiment, this invention provides for the agglomerated products to be left in the secondary drying and cooling area for a period of 10 to 30 minutes, preferably 15 to 25 minutes, wherein the product temperature after leaving the cooling zone is especially in the range of 20° Celsius to 40° Celsius, preferably 25° Celsius to 35° Celsius. The dried agglomerate has a water content of 1.0 wt % to 5 wt %, preferably 1.5 wt % to 3.5 wt %. The degree of crystallization is preferably >50%, especially preferably >70%, and most especially preferably >90%. In an advantageous manner, this leads to avoidance of plastic properties in the end product, which is advantageous for sensory reasons.

Finally, in another preferred embodiment, this invention provides for recrystallization, if performed at all, to be carried out over a period of 1 to 4 hours, preferably 1.5 to 2.5 hours.

It goes without saying that the invention also provides for the agglomerated product obtained after spray drying to be pulverized, e.g., ground and/or screened, e.g., by means of an oscillating screening machine, before, during or after the secondary and/or cooling. This makes it possible to obtain fractions with precisely defined particle sizes, to separate them and then send them for further processing or recycling.

In an advantageous manner in a preferred embodiment, this invention also provides for the portion of the agglomerate which is provided for recycling according to this invention, i.e., the ground, agglomerated and free-flowing product, to be circulated permanently, i.e., continuously, which means that it is added to the educt solution or suspension which is sprayed into it.

In conjunction with the present invention, a compressed product is understood to be a food, pharmaceutical or semi-luxury item consisting of compressed ingredients. A compressed product in the sense of the present invention may be a tablet, for example. The agglomerates produced by the method according to this invention are generally characterized by good free-flowing properties and good self-binding properties that largely or entirely prevent sticking to the press.

The compressed product produced from the raw material according to this invention, i.e., the agglomerate, may also contain additives and auxiliary substances such as lubricants, binders, diluents and flavorings, taste substances, parting compounds, coloring agents, sweeteners and/or pharmaceutical substances. In conjunction with the present invention, the term isomalt is understood to refer to an almost equimolar mixture of the two stereoisomers 6-O-α-D-glucopyranosyl-D-sorbitol (1,6-GPS) and 1-O-α-D-glucopyranosyl-D-mannitol (1,1-GPM), which is also known by the brand name Palatinit®. The term isomalt variant is understood to refer to mixtures containing 1,6-GPS and 1,1-GPM, which are characterized by quantity ratios of 1,1-GPM to 1,6-GPS which deviate from those of isomalt and/or which contain other sugar alcohols such as 1,1-GPS (1-O-α-D-glucopyranosyl-D-sorbitol). Such mixtures are disclosed in European Patent Application 0 625 578 A1, for example, which is thus included in the disclosure content of the present patent application with regard to the quantitative and qualitative composition of the sugar alcohol mixtures containing 1,1-GPM and 1,6-GPS and methods of producing same. Therefore, isomalt variants may include, for example, mixtures of 10 wt % to 50 wt % 1,6-GPS, 2 wt % to 20 wt % 1,1-GPS and 30 wt % to 70 wt % 1,1-GPM, or mixtures of 5 wt % to 10 wt % 1,6-GPS, 30 wt % to 40 wt % 1,1-GPS and 45 wt % to 60 wt % 1,1-GPM. According to the aforementioned, isomalt variants may also include mixtures enriched with 1,6-GPS or 1,1-GPM, i.e., mixtures such as those described in German Patent 195 32 396 C2, which are also included in the disclosure content of the present patent application with regard to the quantitative and qualitative composition of the mixtures described there and methods of producing the same. Mixtures enriched with 1,6-GPS are characterized by a 1,6-GPS content of 57 wt % to 99 wt % and a 1,1-GPM content of 43 wt % to 1 wt %, while mixtures containing 1,1-GPM are characterized by a 1,6-GPS content of 1 wt % to 43 wt % and a 1,1-GPM content of 57 wt % to 99 wt %. The above-mentioned isomalt variants or the isomalt may of course also contain other substances such as mannitol, sorbitol, hydrogenated or non-hydrogenated oligosaccharides as well as optionally glucose, fructose and/or sucrose, trehalulose or isomaltose.

In conjunction with the present invention, a solution or suspension containing isomalt, isomalt variants or isomaltulose is understood to be a solution or suspension of the educt(s) in water.

In another advantageous embodiment of the present teaching, this invention also proposes that size fractionation should be performed following agglomeration, secondary drying and cooling but before compressing the agglomerate, especially by separation of oversized particles and fines from the agglomerated products. A screening machine with a screen lining of 0.8 mm to 0.1 mm, for example, may preferably be used here.

In another process step, it may be provided according to this invention that the agglomerated product, which is optionally also fractionated after agglomeration, is pressed directly, i.e., compressed products are produced. It is also possible to provide here for additives or auxiliary substances such as parting compounds or lubricants, active ingredients or the substances mentioned below, etc. to be added to the agglomerates. Such substances may include flavorings or taste substances, sweeteners, food-compatible acids, disintegrants, coloring agents, vitamins, minerals, sweeteners, active ingredients, which may also be used in a controlled manner with regard to offering advantageous properties, monosaccharides, disaccharides, monosaccharide alcohols, disaccharide alcohols, starch, starch derivatives, pectin, polyvinylpyrrolidone, cellulose, cellulose derivatives, stearic acid or the salts thereof, inulin, oligofructose or functional foods. As an alternative, these additives or auxiliary substances may be added directly to the educt solution or suspension and then spray dried, i.e., added to the educt before production of the agglomerates. Thus, according to this invention, inulin, for example, especially preferably in an amount of up to 30 wt %, may be added to the agglomerate or the educt. Sorbitol, mannitol, hydrogenated or non-hydrogenated oligosaccharides, erythritol, xylitol or sugars such as sucrose, glucose, lactose, fructose or xylose may also be added to the agglomerates or the educt. In an advantageous manner, the proportion of these substances, based on the total dry weight, is less than 30 wt %, preferably less than 25 wt %, 20 wt %, 15 wt %, 10 wt % or 5 wt %. In an especially advantageous embodiment, the compressed products produced according to this invention are sugar-free. In another embodiment, the compress products may be xylitol-free. In another preferred embodiment, the compressed products according to this invention may be low-calorie products, suitable for diabetics, non-cariogenic, bi-fidogenic or anti-lipidemic.

Furthermore, intense sweeteners such as dipeptide sweeteners, saccharine, acesulfame K, aspartame, cyclamate, glycyrrhizine, thaumatin, saccharine, steveoside, neohesperidin dihydrochalcone and/or sucralose may also be added to the agglomerates or the educt. In an advantageous manner, the compressed products according to this invention also contain taste or flavoring substances such as lemon flavoring or peppermint flavoring. The compressed products according to this invention may also contain food-compatible acids such as ascorbic acid or citric acid and also fatty acids or their salts such as magnesium stearate or sodium stearate as lubricants. Finally, the compressed products according to this invention may also contain coloring agents and/or disintegrants such as bicarbonate or carboxymethyl cellulose.

In an especially preferred embodiment, the compressed products that are produced introduce active pharmaceutical ingredients into the mouth and throat area and release them there. In conjunction with the present invention, active pharmaceutical ingredients are understood to refer to substances that have a desired prophylactic or therapeutic effect on the human or animal body. These substances are thus used in particular to prevent or treat deficiency states or disease syndromes. According to this invention, for example, enzymes, coenzymes, minerals, vitamins, antibiotics, microbicidal or fungicidal substances, nicotine, caffeine, zinc, eucalyptus, menthol, codeine, phenacetin, aspirin or other active pharmaceutical substances may be incorporated into the compressed products. The active pharmaceutical ingredients are to be provided in an amount that will have the desired pharmaceutical effect. The processability of the compressed products under gentle conditions makes the compressed products according to this invention especially suitable for introducing active pharmaceutical ingredients into the mouth and throat area.

This invention also relates to the compressed products produced by the method according to this invention, especially in the form of lozenges, effervescent tablets or chewable tablets.

Other advantageous embodiments of this invention are derived from the subclaims.

The following examples are presented to illustrate this invention in detail.

EXAMPLE 1

Production of Agglomerates

The educt used was isomalt (an almost equimolar mixture of 1,1-GPM and 1,6-GPS) and an isomalt variant (composition: 1,1-GPM≈51%; 1,6-GPS≈38%; sorbitol≈4%; mannitol≈2%; others≈5%, each amount in percent by weight [wt %] based on dry solids).

The ingredients were spray dried in a spray belt dryer that included a spray tower and a cloth belt arranged beneath the spray dryer.

At the end of the spray tower, a 60 wt % to 70 wt % solution of the educts (based on the dry solids) (temperature of the product solution: 65° Celsius to 80° Celsius) and ground dry product (grain size 100 to 300 µm) were supplied in such a way as to yield the most thorough possible mixing of the solution and the powder. The spray pressure of the educt solution was 120 to 180 bar. The quantity ratio of powder to educt solution was 3:1. In co-current with the former, drying air was supplied at a temperature of 140° Celsius to 160° Celsius. During the time of fall in the spray tower, the water of the educt solution evaporated and a product layer consisting of agglomerate was deposited on the cloth belt. The cloth belt conveyed the agglomerate into a downstream secondary drying and cooling zone, which was acted upon by secondary drying and cooling air at a temperature of 20° Celsius to 60° Celsius. The product remained in the secondary drying and cooling zone for 15 to 25 minutes and had a temperature of 25° Celsius to 35° Celsius after leaving the cooling zone.

A secondary crystallization could optionally be carried out in a drum, preferably with an average dwell time of 1.5 to 2.5 hours. Then the product was partially ground and was conveyed back to the spray tower in the form bf a fine powder having a particle diameter of 30 to 300 µm; in the spray tower, it was brought in contact with educt solution sprayed into the spray tower. Another portion was removed from circulation, bagged and processed further.

The resulting agglomerates were fractionated by means of an oscillating screening machine from the Allgaier company with a screen lining of 0.8 mm to 0.1 mm. Screen fractions of the following grain sizes were produced:

0.10 to 0.20 mm 0.20 to 0.30 mm 0.30 to 0.40 mm 0.40 to 0.50 mm 0.50 to 0.63 mm 0.10 to 0.63 mm.

Compressed product recipes containing these fractions were designated in the following table as 01-02, 02-03, 03-04, 04-05, 05-06, 01-06.

The resulting fractions were prepared according to the following recipe to yield compressed product mixtures:

Recipe:

| | |
|---|---|
| Isomalt or isomalt variant | 98.41% |
| Mg stearate | 0.50% |
| Menthol L | 0.30% |
| Peppermint flavor | 0.80% |
| Acesulfame K | 0.15% |
| Aspartame | 0.15% |

All the amounts are given in wt %, based on the total dry weight of the compressed product.

Table 1 below shows physicochemical parameters of the compressed product mixtures used here.

TABLE 1

| Recipe | Water content % | $d_{05}$ mm | $d_{95}$ mm | d mm | n | Bulk density g/cm³ | Tamped density g/cm³ | Flow time s |
|---|---|---|---|---|---|---|---|---|
| 1. Isomalt 01–02 | 2.5 | 0.33 | 0.19 | 0.27 | 5.3 | 0.59 | 0.6 | 2.6 |
| 1. Isomalt 02–03 | 2.5 | 0.36 | 0.22 | 0.32 | 8.2 | 0.54 | 0.55 | 2.9 |
| 1. Isomalt 03–04 | 2.5 | 0.45 | 0.25 | 0.38 | 6.9 | 0.53 | 0.53 | 3.0 |
| 1. Isomalt 04–05 | 2.5 | 0.5 | 0.3 | 0.44 | 8.1 | 0.49 | 0.49 | 3.0 |
| 1. Isomalt 05–06 | 2.5 | 0.5 | 0.3 | 0.44 | 8.1 | 0.49 | 0.49 | 2.8 |
| 1. Isomalt 01–06 | 2.5 | 0.46 | 0.18 | 0.36 | 4.4 | 0.52 | 0.53 | 3.5 |
| 2. Isomalt 01–06 | 2.6 | 0.35 | 0.17 | 0.29 | 5.6 | 0.56 | 0.56 | 3.6 |
| 2. Isomalt 02–03 | 2.5 | 0.39 | 0.2 | 0.33 | 6.1 | 0.54 | 0.55 | 4.6 |
| 2. Isomalt 03–04 | 2.6 | 0.49 | 0.28 | 0.41 | 7.3 | 0.52 | 0.53 | 3.2 |
| 2. Isomalt 04–05 | 2.6 | 0.5 | 0.34 | 0.45 | 10.1 | 0.49 | 0.49 | 3.0 |
| 2. Isomalt 05–06 | 2.8 | 0.6 | 0.38 | 0.53 | 8.7 | 0.47 | 0.47 | 11.7* |
| 2. Isomalt 01–06 | 2.6 | 0.45 | 0.23 | 0.38 | 6.1 | 0.53 | 0.54 | 2.9 |

Table:
- (1. isomalt (approx. equimolar ratio of GPM and GPS);
- 2. isomalt approx. 51% 1,1-GPM, approx. 38% 1,6-GPS, approx. 4% sorbitol, approx. 2% mannitol, approx. 5% other)).

Determination of the pourability and flow time according to DIN 53194 and DIN 53492.

Type of nozzle for determining pourability:
15 mm diameter: *,
otherwise 25 mm diameter.

Determination of the bulk density and the tamped density[1] according to DIN 53194.

[1]Translator's note: "Stampfdichtigkeit" appears to be a typographical error for "Stampfdichte" as used elsewhere in this text.

The above-mentioned mixtures for the compressed product experiments were produced in the ploughshare mixer from the Lödige company. The mixing time was 1.5 minutes. The individual ingredients were added through an opening in the cover flap on the mixer. The liquid ingredient (peppermint flavoring) was added through an atomization system. After the end of the mixing operation, the mixtures were poured into PE bags of 5 kg each and welded.

Then with the resulting mixtures, round tablets with a diameter of 18 mm and having facets, a web height of 0.35 to 0.37 mm and a weight between 850 mg and 1000 mg are produced by using a Fette PT 2090 rotary press.

EXAMPLE 2

Comparison of Breaking Force

Table 2 below shows a breaking force comparison between isomalt FE (related art) and the compressed products of isomalt according to this invention (first isomalt 03-04) and an isomalt variant (second isomalt 03-04) (see Table 1). It is found that considerably more stable compressed products can be obtained at the same compression force by using agglomerates produced according to this invention.

Comparison of breaking force with isomalt type FE and agglomerated products

TABLE II

| | Isomalt type FE* (d 95 approx. 300 μm) | 1. Isomalt 03–04 (d 95 = 0.25 μm) | 2. Isomalt 03–04 (d 95 = 0.28 μm) |
|---|---|---|---|
| Breaking force in N | 62 | 201 | 220 |
| Pressure force in kN | 50 | 50 | 50 |

*Related art.

What is claimed is:

1. A method of producing an agglomerated, free-flowing product selected from the group consisting of isomaltulose, isomalt and an isomalt variant, wherein a solution or suspension containing at least one product selected from the group consisting of isomaltulose, isomalt, and an isomalt variant is sprayed with a supply of dry air into a powder selected from the group consisting of isomaltulose, isomalt, and an isomalt variant, and the resulting agglomerated product is subjected to a secondary drying and cooling, and an agglomerated free-flowing product is obtained.

2. The method according to claim 1, wherein secondary crystallization takes place following cooling of the secondary dried product.

3. The method according to claim 1, wherein at least a portion of the resulting agglomerated free-flowing product is ground following the cooling or secondary crystallization.

4. The method according to claim 3, wherein a portion of the ground powder is introduced back into the process in the form of an educt.

5. The method according to claim 1, wherein the solution or suspension has a dry solids content of 30 wt % to 70 wt %.

6. The method according to claim 1, wherein the solution or suspension has a temperature of 50° Celsius to 90° Celsius.

7. The method according to claim 1, wherein the solution or suspension is sprayed into the powder at a spray pressure of 100 bar to 200 bar.

8. The method according to claim 1, wherein the powder has a particle size of 50 μm to 400 μm.

9. The method according to claim 1, wherein the quantity ratio of powder to educt solution or suspension amounts to 1:1 to 3.5:1.

10. The method according to claim 1, wherein the drying air has a temperature of 120° Celsius to 180° Celsius.

11. The method according to claim 1, wherein the secondary drying and cooling take place with a supply of air at a temperature of 20° Celsius to 80° Celsius.

12. The method according to claim 1, wherein the secondary drying and cooling take place over a period of 10 to 30 minutes.

13. The method according to claim 1, wherein the secondary crystallization takes place over a period of one to four hours.

14. The method according to claim 1, wherein the solution or suspension containing the isomaltulose, isomalt or an isomalt variant together with additives, auxiliary substances, active ingredients, parting compounds, lubricants, flavorings, sweeteners, food-compatible acids, disintegrants or coloring agents is spray dried.

15. An agglomerate producible according to the method of any one of the preceding claims.

16. The method of producing a compressed product, wherein a method is carried out according to claim 1, and the resulting agglomerate is pressed to form a compressed product.

17. The method according to claim 16, wherein additives, auxiliary substances, active ingredients, parting compounds, lubricants, flavorings, sweeteners, food-compatible acids, disintegrants or coloring agents are added to the agglomerate before pressing.

18. A compressed product producible according to one of the method of claim 16 or 17.

* * * * *